United States Patent
Henkel et al.

(10) Patent No.: US 10,836,716 B2
(45) Date of Patent: Nov. 17, 2020

(54) PROCESS FOR THE CONTINUOUS PRODUCTION OF ALKALI SALTS OF THE DIALKYLDITHIOCARBAMIC ACID

(71) Applicant: EPC Engineering & Technologies GMBH, Arnstadt (DE)

(72) Inventors: Jens Henkel, Meuselbach-Schwarzmuhle (DE); Jurgen Rassbach, Arnstadt (DE); Tobias Przynosz, Saalfeld (DE)

(73) Assignee: EPC ENGINEERING & TECHNOLOGIES GMBH (DE)

( * ) Notice: Subject to any disclaimer, the term of this patent is extended or adjusted under 35 U.S.C. 154(b) by 0 days.

(21) Appl. No.: 16/500,987

(22) PCT Filed: Apr. 10, 2018

(86) PCT No.: PCT/EP2018/059204
§ 371 (c)(1),
(2) Date: Oct. 4, 2019

(87) PCT Pub. No.: WO2018/189204
PCT Pub. Date: Oct. 18, 2018

(65) Prior Publication Data
US 2020/0031768 A1    Jan. 30, 2020

(30) Foreign Application Priority Data
Apr. 12, 2017  (DE) .................. 10 2017 107 932

(51) Int. Cl.
C07C 327/18    (2006.01)
(52) U.S. Cl.
CPC .................. *C07C 327/18* (2013.01)
(58) Field of Classification Search
CPC ........................ C07C 327/18; C07C 333/16
See application file for complete search history.

(56) References Cited

U.S. PATENT DOCUMENTS 2,563,007 A * 8/1951 Crouch ................ C07C 333/16
544/161

FOREIGN PATENT DOCUMENTS

| DE | 19930625 A1 |   | 1/2001 |
|----|-------------|---|--------|
| FR | 1168420     | * | 12/1958 |
| FR | 1168420 A   |   | 12/1958 |
| GB | 1020746 A   |   | 2/1966 |
| RU | 2248968 C1  |   | 3/2005 |

OTHER PUBLICATIONS

International Search Report (English Translation, PCT/EP2018/059204, dated Oct. 18, 2018.
Witten Opinion of the International Search Authority, PCT/EP2018/059204, dated Oct. 18, 2018.
Mousami Sharma et al. "Preparation and Characterization of the Adducts of Bis(N,N-diethyldithicarbamato) oxovanadium(IV) and Copper(II) with n-Propylamine and Isopropylamine" Chemical Science Transactions, vol. 2, No. 2, Apr. 18, 2018, pagres 367-374 DOI:10.7598/cst2013.265 ISSN: 2278-3458, XP055480065.
Qin Yukun et al. "Synthesis of chitosan derivative with diethyldithicarbamate and its antifungal activity" International Journal of Biological Macromolecules, vol. 65, 2014, pp. 369-374 DOI: 10.1016/J.IJBIOMAC.2014.01.072 ISSN: 0141-8130, XP028631065.

* cited by examiner

*Primary Examiner* — Paul A Zucker
(74) *Attorney, Agent, or Firm* — Winstead PC

(57) ABSTRACT

An exemplary process for the production of alkali metal salts of dialkyldithiocarbamic acids produced according to the following steps: i) reaction of one or more dialkylamines, carbon disulphide and alkali metal hydroxides to form alkali metal salts of dialkyldithiocarbamic acids; ii) crystallisation to form a crystal suspension of alkali metal salts of dialkyldithiocarbamic acids; iii) separation of crystals of alkali metal salts of dialkyldithiocarbamic acids from the mother liquor in step ii; (iv) recirculation of the separated mother liquor into the crystallisation process; and v) drying of the alkali metal salts of dialkyldithiocarbamic acids.

14 Claims, 1 Drawing Sheet

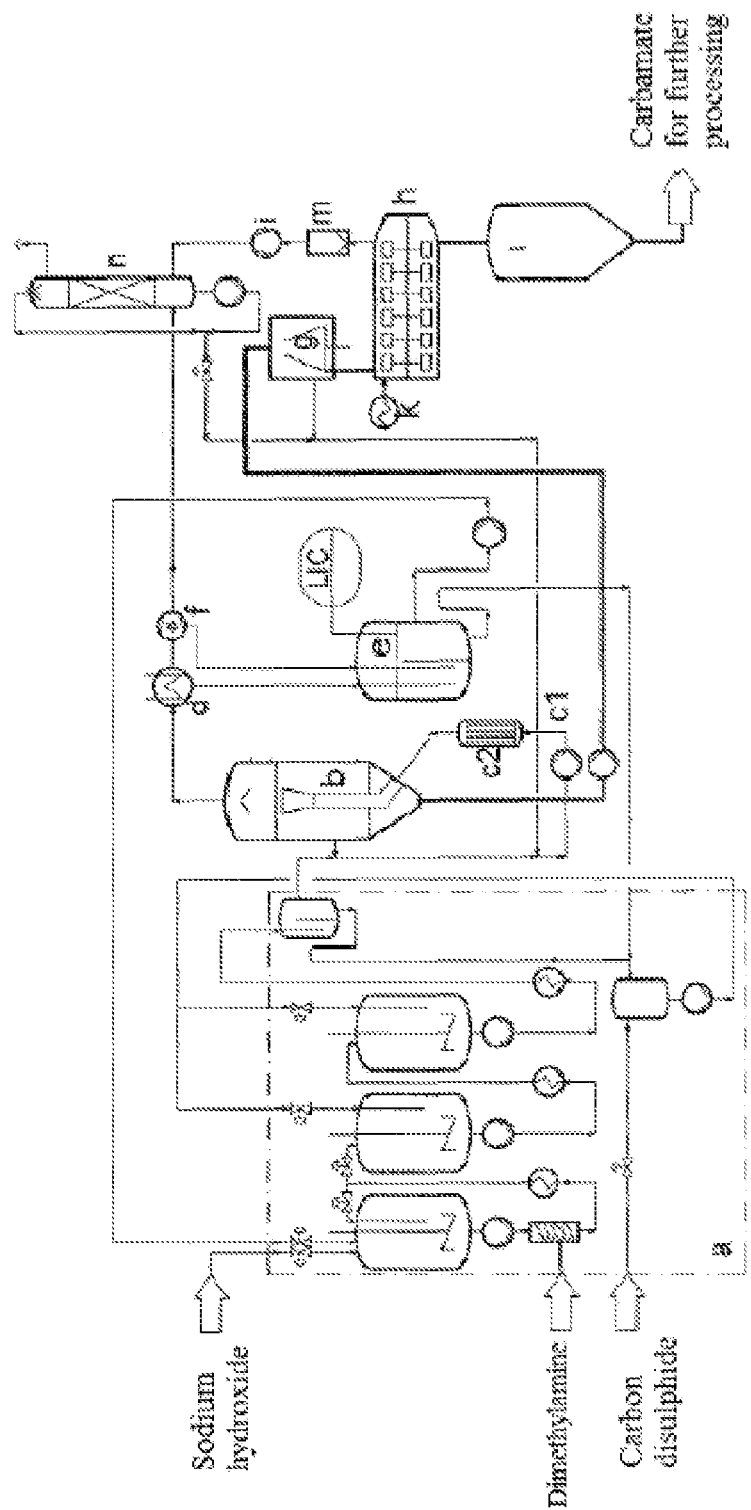

PROCESS FOR THE CONTINUOUS PRODUCTION OF ALKALI SALTS OF THE DIALKYLDITHIOCARBAMIC ACID

BRIEF DESCRIPTION OF DRAWING

The drawing illustrates a process flow diagram for an embodiment of a process according to the invention.

The present invention relates to a process for the production of alkali metal salts of dialkyldithiocarbamic acids and to alkali metal salts of dialkyldithiocarbamic acids produced according to said process.

Salts of dithiocarbamic acids are referred to as dithiocarbamates. The general structural formula of such compounds is reproduced below.

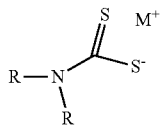

Especially, the alkali metal salts of the dithiocarbamic acids have a wide range of applications. For example, they are used in the agricultural sector as fungicides, herbicides and insecticides. Another application is the use in chemical synthesis. In addition, alkali metal salts of dithiocarbamic acids are also used as vulcanisation accelerators for synthetic rubbers. Another field of application, especially for sodium dimethyldithiocarbamate, is the use as a depressant in the froth flotation of nickel ores and as a non-cyanide auxiliary in the froth flotation of sulphide ores.

An important process for producing alkali metal salts of the dithiocarbamic acids uses the reaction of ammonia or primary or secondary amines with carbon disulphide and alkali metal hydroxide. This reaction will be presented hereinafter by way of example on the basis of the synthesis of sodium dialkylcarbamates from dialkylamines, carbon disulphide, and sodium hydroxide:

$$R_2NH + CS_2 + NaOH \rightarrow R_2NCS_2^- Na^+ + H_2O$$

The reaction may take place in the liquid phase (DDR Patent No. 241737) or with contact of a liquid phase with a vapour or gas phase (DBP 1118186).

The obtained aqueous solutions of the particular alkali salt of the dialkyldithiocarbamic acid are fully evaporated under vacuum, which entails a high energy input and long residence times.

A process which contains a crystallisation stage, wherein toluene is used in mixture with water as solvent, is also known. A disadvantage here is the use of toluene, which is highly flammable, toxic for reproduction, harmful to health, and an irritant.

The previously known processes thus suffer from the disadvantage that they either are laborious and have a high energy input, or that they use organic solvents for precipitation of the alkali metal salts of the dithiocarbamic acids, which is questionable from an environmental viewpoint and also from the viewpoint of occupational safety. Both a high energy input and the use of organic solvents, which necessitate a complex processing of the wastewater, lead to economic disadvantages. In addition, many production processes for the alkali metal salts of dithiocarbamic acids known in the prior art may not be conducted as continuous processes.

Against this background, the aim of the present invention was to provide a process for producing alkali metal salts of dialkyldithiocarbamic acids which has a minimal energy input and at the same time restricts the handling of hazardous substances to the unavoidable compounds carbon disulphide and dialkylamine. In addition, waste products in the form of gases, liquids and solids should be avoided to the greatest possible extent. Furthermore, the aim of the present invention was to provide a process for producing alkali metal salts of dialkyldithiocarbamic acids which has closed material cycles as far as possible and in which the resultant wastewater is purified with minimal effort to such an extent that all legal limits may be observed as economically as possible.

The aim according to the invention is achieved by a process for producing alkali metal salts of dialkyldithiocarbamic acids comprising the following steps:

i) a reaction step in the form of the reaction of one or more dialkylamines, carbon disulphide and one or more alkali metal hydroxides in aqueous solution so as to form an aqueous reaction solution of alkali metal salts of dialkyldithiocarbamic acids;

ii) a crystallisation step in the form of the introduction of the reaction solution from step i) in an evaporative crystalliser, which is heated by a heater such that a temperature of approximately 30-95, especially 45-80° C. is present at the contact surface of the heating element to the reaction solution, and in which a pressure of approximately 10-800 mbar (a), preferably 50-400 mbar (a) is present, so as to form a crystal suspension of alkali metal salts of dialkyldithiocarbamic acids;

iii) a separation step in the form of the introduction of the crystal suspension formed in step ii) into a centrifuge and centrifugation of the crystal suspension for solid/liquid separation so as to form crystals of alkali metal salts of dialkyldithiocarbamic acids on the one hand and separated mother liquor on the other hand;

iv) a recirculation step in the form of the recirculation of the separated mother liquor obtained in step iii) into the crystallisation process;

v) a drying step in the form of the drying of the alkali metal salts of dialkyldithiocarbamic acids separated off in step iii), wherein the drying step is designed especially such that the separated alkali metal salts of the dialkyldithiocarbamic acids are dried by means of a contact dryer.

By way of the combination of steps ii) (crystallisation step) and iii) (separation step) in the form according to the invention it is possible to obtain alkali metal salts of dialkyldithiocarbamic acids in crystalline form with low energy demand and without the use of organic solvents, such as toluene. If the temperature and pressure conditions for the evaporative crystalliser as defined in step ii) are observed, a crystal suspension of alkali metal salts of dialkyldithiocarbamic acids may be obtained very quickly. This makes it possible to carry out the process according to the invention as a continuous process.

By way of step iv) (recirculation step) in the form of the recirculation of the separated mother liquor obtained in step iii) (separation step) into the crystallisation process, the process may be carried out very efficiently, since the alkali metal salt of the dialkyldithiocarbamic acids still present in the mother liquor is not lost.

In a preferred embodiment the reaction step i) is performed such that the reaction step comprises at least three reaction stages.

Although the process according to the invention is not limited to certain alkali metal salts, the alkali metal salts are preferably sodium salts or potassium salts.

Due to the great economic significance of these compounds, the process according to the invention is preferably carried out such that one or more of sodium dimethyldithiocarbamate, sodium diethyldithiocarbamate and potassium dimethyldithiocarbamate is/are formed as alkali metal salt of dialkyldithiocarbamic acids.

In an especially preferred embodiment the process according to the invention is performed as a continuous process.

A disadvantage of the processes known from the prior art lies in that fact that wastewater and waste gases are created, which contain constituents that are toxic and/or harmful to the environment. In order to overcome this disadvantage, the process according to the invention is preferably performed such that exhaust vapours formed in the crystallisation step ii) are condensed to form a vapour condensate.

It is especially preferred that, after the condensation of the exhaust vapours to form a vapour condensate, any remaining inert waste gases are washed with water in a waste gas scrubbing, and the washing water is fed back into the reaction step i).

By way of this recirculation of the washing water into the reaction step i), it is possible to feed back the reactants dissolved in the washing water, and possibly products, into the reaction process. On the one hand this increases the yield of the process and at the same time loaded waste gases are avoided.

It is preferably preferred that the recovered vapour condensate is also fed back into the reaction step i).

This vapour condensate likewise contains reactants and possibly products of the reaction and may thus be re-used.

In an especially preferred embodiment the process according to the invention is performed such that the dry step is carried out in the contact dryer at a temperature of 30-110° C., especially 60-100° C., and at a pressure of 5-1000 mbar (a), preferably 50-200 mbar (a), more preferably 60-80 mbar (a).

It has been found that, if these parameters for temperature and pressure are observed, a very efficient drying of the crystal suspension is possible. It is especially preferred that the dry step is carried out such that inert, pre-heated carrier gas is conducted through the contact dryer.

The use of a pre-heated carrier gas enables a very quick transfer of the crystal suspension into dry crystals. Whereas the choice of the used carrier gas is not subject to any fundamental restrictions, it is especially preferred that the carrier gas is selected from air and/or nitrogen.

On account of the oxidation sensitivity of the alkali metal salts of dialkyldithiocarbamic acids, which is not excessively high, it is often possible to use air, which is considerably more cost-effective, as carrier gas.

In order to enable closed material circuits wherever possible, the process according to the invention is configured in a preferred embodiment such that the carrier gas, after having been conducted through the contact dryer, is washed with water in a waste gas scrubbing, and the washing water is fed back into the reaction step i).

As a result of this further recirculation step, on the one hand the carrier gas may be largely purified and on the other hand reactants dissolved out therefrom, and possibly products, may be recirculated in the form of the washing water into the process.

In an especially preferred embodiment the process according to the invention is configured such that the reaction step i) comprises at least three reaction stages.

In a further especially preferred embodiment the process according to the invention is configured such that the individual reaction partners in the reaction step i) are fed into the reaction stages in static mixers, the pressure in the static mixer being greater than the vapour pressure of the particular reaction partner.

An especially preferred embodiment of the process according to the invention is described in the drawing (process flow diagram) on the basis of the example of the production of alkali metal salts, for example sodium salts, of dialkyldithiocarbamic acids, for example dimethyldithiocarbamic acid.

In the reaction stage a, an aqueous solution of the alkali salt of the dialkyldithiocarbamic acids, for example sodium dimethyldithiocarbamate, is produced from dialkylamine, for example dimethylamine and carbon disulphide, in the presence of a lye, for example sodium hydroxide. The solution of the product is diluted on account of the water which on the one hand is introduced with the sodium hydroxide and the dialkylamine and on the other hand is created during the reaction.

The solution passes into the evaporation crystalliser (b) via the circulation evaporator, which comprises the recirculation pump (c1) and the heater (c2), and is heated to boiling point. The boiling solution passes into the crystalliser (b), where the vapour and liquid phase are separated.

The liquid is circulated, and the vapour leaves the crystalliser (b) through the condenser (d). Condensable constituents (water and carbon disulphide) condense and are removed via a barometric tail pipe (e). Non-condensable constituents pass via the vacuum pump (f) to waste gas purification. By way of the evaporation and the associated concentration of the product solution, part of the, for example, sodium dimethyldithiocarbamate crystallises as solid substance. The crystal suspension is removed in part and fed to the centrifuge (g). Here, the solid substance is separated off approximately quantitatively and passes with a residual moisture, which corresponds to a substance amount fraction of 65%-75% (mol/mol) water, to the dryer (h). Here, the surface moisture is evaporated, but the water of crystallisation is preserved.

The separated liquid (mother liquor) is fed back into the crystalliser. The crystals pre-dried in this way pass into a contact dryer (h) (for example paddle dryer), which is heated to temperatures between 60 and 100° C. by means of vapour or thermal oil. The exhaust vapours are drawn off by means of a vacuum pump (i). In order to support the drying, a carrier gas flow pre-heated via the air pre-heater (k) is fed.

The dried product is discharged into an intermediate silo (l) for processing (for example cooling and/or packaging).

The waste air of the dryer passes via a particle filter (m) to a scrubber (n), which washes out the dust particles from the waste gas by means of water. The washing water is fed back together with some of the vapour condensate into the reaction stage. Excess water is subjected to a wastewater purification.

The process according to the invention is also applicable for alkali metal salts of dialkyldithiocarbamic acids produced according to the above-described process.

Although the alkali metal salts according to the invention are not limited to certain alkali metals, they are preferably sodium or potassium salts of dialkyldithiocarbamic acid. The alkali metal salts of dialkyldithiocarbamic acids according to the invention are especially preferably one or more of sodium dimethyldithiocarbamate, sodium diethyldithiocarbamate, and potassium dimethyldithiocarbamate.

The alkali metal salts of dialkyldithiocarbamic acids according to the invention are especially preferably present in the form of crystalline solid substance, wherein in a preferred embodiment they contain more than (1 mol water)/(mol alkali metal salt) of water of crystallisation.

The invention claimed is:

1. A process for producing alkali metal salts of dialkyldithiocarbamic acids, comprising the steps:
   i) a reaction step comprising a reaction of one or more dialkylamines, carbon disulphide and one or more alkali metal hydroxides in aqueous solution so as to form an aqueous reaction solution of alkali metal salts of dialkyldithiocarbamic acids;
   ii) a crystallisation step comprising an introduction of the reaction solution from step i) in an evaporative crystalliser, which is heated by a heater such that a temperature of 30-95° C. is present at the contact surface of the heating element to the reaction solution, and in which a pressure of 10-800 mbar is present, so as to form a crystal suspension of alkali metal salts of dialkyldithiocarbamic acids;
   iii) a separation step comprising an introduction of the crystal suspension formed in step ii) into a centrifuge and centrifugation of the crystal suspension for solid/liquid separation so as to form crystals of alkali metal salts of dialkyldithiocarbamic acids on the one hand and separated mother liquor on the other hand;
   iv) a recirculation step comprising a recirculation of the separated mother liquor obtained in step iii) into the crystallisation process; and
   v) a drying step comprising a drying of the alkali metal salts of dialkyldithiocarbamic acids separated off in step iii), wherein the drying step is designed especially such that the separated alkali metal salts of the dialkyldithiocarbamic acids are dried by means of a contact dryer.

2. A process according to claim 1, characterised in that one or more of one or more of sodium dimethyldithiocarbamate, sodium diethyldithiocarbamate and potassium dimethyldithiocarbamate is/are formed as alkali metal salt of dialkyldithiocarbamic acids.

3. A process according to claim 1, characterised in that the process is performed as a continuous process.

4. A process according to claim 1, characterised in that exhaust vapours formed in the crystallisation step ii) are condensed to form a vapour condensate.

5. A process according to claim 4, characterised in that, after the condensation of the exhaust vapours to form a vapour condensate, any remaining inert waste gases are washed with water in a waste gas scrubbing, and the washing water is recirculated into the reaction step i).

6. A process according to claim 5, characterised in that the vapour condensate is fed back into the reaction step i).

7. A process according to claim 1, characterised in that the process is performed such that the drying step is carried out in the contact dryer at a temperature of 30-110° C., and at a pressure of 5-1000 mbar.

8. A process according to claim 7, characterised in that the drying step is carried out such that inert, pre-heated carrier gas is conducted through the contact dryer.

9. A process according to claim 8, characterised in that the carrier gas is selected from air and/or nitrogen.

10. A process according to claim 8, characterised in that the carrier gas, after having been conducted through the contact dryer, is washed with water in a waste gas scrubbing, and the washing water is fed back into the reaction step i).

11. A process according to claim 1, characterised in that the individual reaction partners in the reaction step i) are fed into a static mixer, the pressure in the static mixer being greater than the vapour pressure of the particular reaction partner.

12. A process according to claim 1, wherein a temperature of 45-80° C. is present at the contact surface of the heating element to the reaction solution, and in which a pressure of 50-400 mbar is present.

13. A process according to claim 1, characterised in that the process is performed such that the dry step is carried out in the contact dryer at a temperature of 60-100° C. and at a pressure of 50-200 mbar.

14. A process according to claim 1, characterised in that the process is performed such that the dry step is carried out in the contact dryer at a temperature of 60-100° C. and at a pressure of 60-80 mbar.

* * * * *